United States Patent
Chen et al.

(10) Patent No.: US 8,232,048 B2
(45) Date of Patent: Jul. 31, 2012

(54) HYBRIDOMA CELL LINE PRODUCING MONOCLONAL ANTIBODY AGAINST FOOT-AND-MOUTH DISEASE VIRUS, THE MONOCLONAL ANTIBODY THEREFROM, IMMUNOASSAY REAGENT AND KIT, AND IMMUNOASSAY METHOD

(75) Inventors: Tsu-Han Chen, Danshui Township, Taipei County (TW); Fan Lee, Danshui Township, Taipei County (TW); Chu-Hsiang Pan, Danshui Township, Taipei County (TW); Ming-Hwa Jong, Danshui Township, Taipei County (TW)

(73) Assignee: Animal Health Research Institute, Council of Agriculture, Executive Yuan, Taipei County (TW)

( * ) Notice: Subject to any disclaimer, the term of this patent is extended or adjusted under 35 U.S.C. 154(b) by 14 days.

(21) Appl. No.: 12/835,412

(22) Filed: Jul. 13, 2010

(65) Prior Publication Data

US 2011/0014639 A1    Jan. 20, 2011

(30) Foreign Application Priority Data

Jul. 14, 2009   (TW) ............................... 98123672 A

(51) Int. Cl.
| | |
|---|---|
| *C12Q 1/70* | (2006.01) |
| *C12N 5/12* | (2006.01) |
| *C07K 16/08* | (2006.01) |

(52) U.S. Cl. ..................... 435/5; 435/339; 530/388.3
(58) Field of Classification Search ............ None
See application file for complete search history.

(56) References Cited

U.S. PATENT DOCUMENTS

| 6,048,538 A | 4/2000 | Yi Wang et al. |
| 2006/0127885 A1 | 6/2006 | Kang et al. |
| 2008/0280296 A1 | 11/2008 | Chen et al. |

FOREIGN PATENT DOCUMENTS

| KR | 2003-0052857 | * | 6/2003 |
| TW | I276686 | | 1/2005 |

OTHER PUBLICATIONS

Grubman et al (Virology 158:133-140, 1987).*
Sorensen et al (Archives of Virology 150:805-814, 2005).*

* cited by examiner

*Primary Examiner* — Mary E Mosher
(74) *Attorney, Agent, or Firm* — Ming Chow; Sinorica, LLC

(57) ABSTRACT

Provided herein are a hybridoma cell line producing monoclonal antibody against foot-and-mouth disease virus (FMDV), the monoclonal antibody therefrom, reagent and kit for ELISA, and immunoassay method. The hybridoma cell line CmA40 as deposited under American Type Culture Collection patent deposit number PTA-11304 is produced by cell fusion of a parental cell and a myeloma cell line. The parental cell is a splenocyte isolated from the spleen of a mouse immunized by an antigen derived from a 3ABC non-structural protein (NSP) of FMDV. The antigen used here is expressed by a prokaryotic cell. The monoclonal antibody produced by the hybridoma cell line CmA40 as deposited under American Type Culture Collection patent deposit number PTA-11304 can specifically recognize a 3ABC polypeptide and does not cross-react with an antiserum of swine vesicular disease virus.

10 Claims, 1 Drawing Sheet

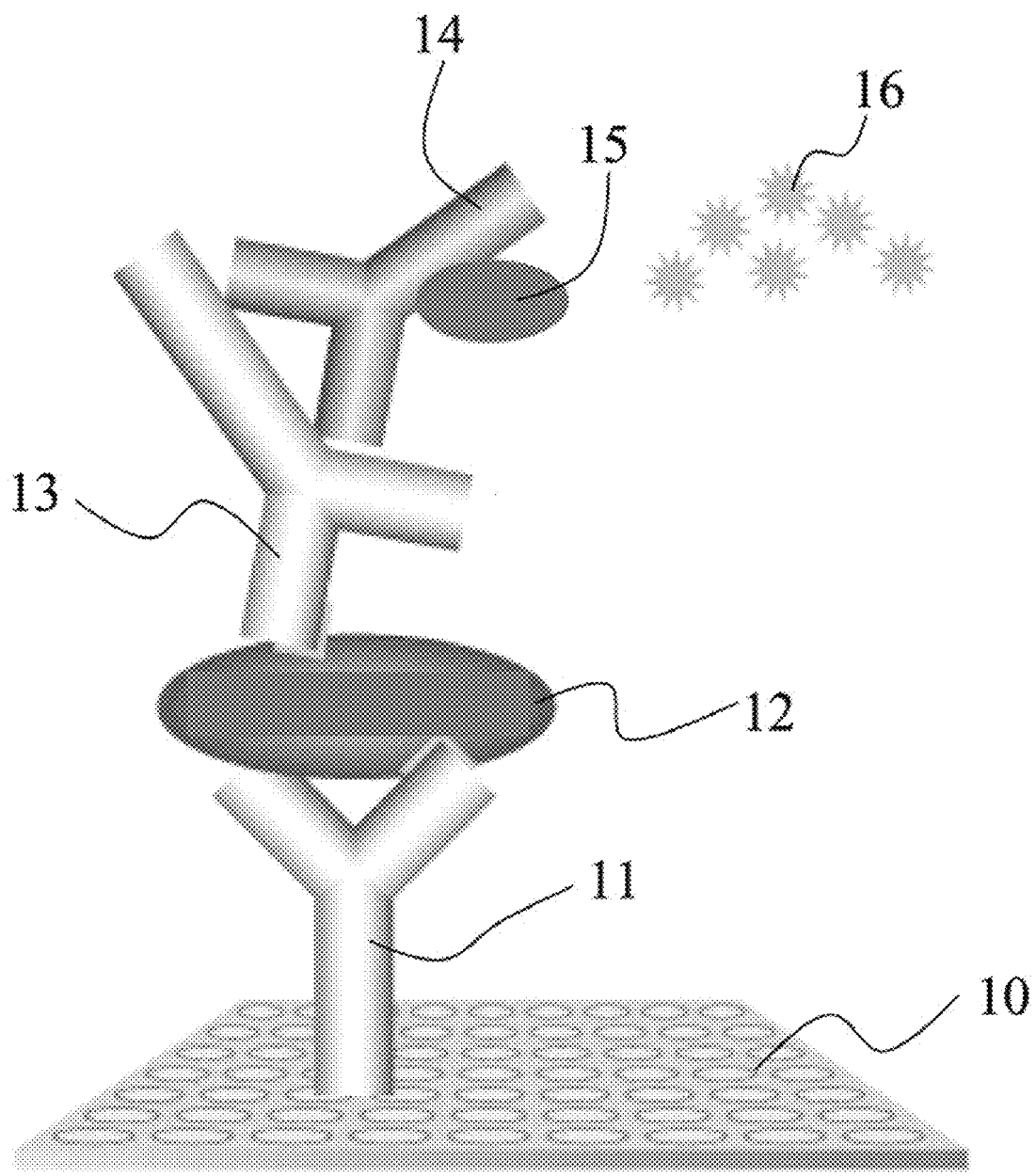

HYBRIDOMA CELL LINE PRODUCING MONOCLONAL ANTIBODY AGAINST FOOT-AND-MOUTH DISEASE VIRUS, THE MONOCLONAL ANTIBODY THEREFROM, IMMUNOASSAY REAGENT AND KIT, AND IMMUNOASSAY METHOD

BACKGROUND OF THE INVENTION

1. Field of the Invention

The present invention relates to a hybridoma cell line producing a monoclonal antibody against foot-and-mouth disease virus (FMDV), the monoclonal antibody therefrom, a reagent and kit for enzyme-linked immunosorbent assay (ELISA), and an immunoassay method. More particularly, the present invention relates to a hybridoma cell line applicable to sandwich ELISA and capable of producing an anti-FMDV NSP (Non-structural protein) monoclonal antibody, the monoclonal antibody therefrom, and an immunoassay reagent and kit including the monoclonal antibody.

2. Description of the Prior Art

Foot-and-mouth disease (FMD) is one of the most contagious diseases among artiodactyla, primarily infecting farm animals such as cows, pigs, and sheep. Typical symptoms of FMD are fever, and formation of epithelial blisters and subsequent necrosis thereof affecting the mouth, tongue, nostrils, legs, and nipples. The foot-and-mouth disease virus, a positive strand RNA virus known as *Aphthovirus, Picornaviridae* in taxonomy, is a tiny non-enveloped virus that has 8.5 kbp of genome translatable into structural proteins (SPs) and non-structural proteins (NSPs). There are seven FMDV serotypes, known as serotypes O, A, C, Asia 1, SAT 1, SAT 2, and SAT 3 (SAT=Southern African Territories), recognized worldwide. The serotypes do not provide cross protection for each other. FMDV mutates quickly and hence presents genetic and antigenic variation between strains. VP1 structural protein on the surface of FMDV shows major neutralization activity with high plasticity and marked antigenic variation. In 1997, heath crisis of Taiwan's animal populations triggered by an outbreak of serotype O FMD epidemic; and the serotype O FMDV was named O/TAW/97. This strain is a prototype of atypical porcinophilic infection in swine. According to experiment results, the codon of a segment (93-102) within the non-structural protein region 3A of the strain is deleted and the segment is a major factor in restricting the growth and replication of the virus in bovine epithelial cells in vitro. Hence, the deletion of the virus strain is proved to be the cause of a lack in bovine susceptibility to the O/TAW/97 strain. The 1997's FMD epidemic in Taiwan caused a great economic loss (estimated at more than US$ 6 billions) because of control measures and trade restrictions. Another virus strain, which was discovered in subclinically infected cattle in Kinmen, has a gene structure with a full-length 3A non-structural protein translation region, and thus is proved to be a pernicious bovine virus strain (O/TAW/2/99). The O/TAW/2/99 strain, which is a topotype of the serotype O FMDV prevalent in southern Asia, launched its first invasion into Taiwan in 1999. Upon the FMD outbreak, the Taiwanese government took quarantine measures immediately, screened animals in the affected farms for FMDV, humanely killed any infected animals promptly, and disposed of the carcasses without delay. In addition, the Taiwanese government carried out precautionary screening of farms suspected of FMDV infection, as an action taken to confine the spread of FMDV.

The conventional ways of producing inactivated viruses have the following drawbacks: (1) With FMD being a highly contagious airborne disease, and the production of inactivated FMDV entailing the use of viruses, the laboratories where inactivated FMDV is to be produced must be Class III negative pressure laboratories conforming to corresponding biosafety specifications, and nevertheless there is a risk that FMDV may be released in the course of production; (2) An inactivated virus cannot produce the non-structural protein which would otherwise be produced naturally by an infected living host, and in consequence a diagnostic immunoassay using the inactivated virus as antigen is unable to distinguish infected living host from vaccinated ones.

SUMMARY OF THE INVENTION

The present invention discloses using *E. coli* cells to express a non-structural protein (NSP) of foot-and-mouth disease virus (FMDV), producing a hybridoma cell line by cell fusion of a parental cell and a myeloma cell line, applying a 3ABC gene of O/TAW/99 to a pET carrier for cloning, using *E. coli* in protein expression, and using a purified NSP as an antigen in enzyme-linked immunosorbent assay (ELISA). The present invention is characterized in that an NSP antibody produced by an animal infected with FMDV can be specifically recognized. The present invention is directed to the following subject matters: an FMDV NSP-specific hybridoma cell line and a monoclonal antibody thereof, and a sandwich ELISA immunoassay reagent or kit including the monoclonal antibody.

To enhance safety and efficacy, the present invention does not involve using viruses. Instead, an antibody is produced, using molecular biology techniques, from hybridoma which is developed by using antigenic determinant sites of a recombinant non-structural protein (RNSP). Since the present invention dispenses with the use of viruses, the present invention is safe and applicable to Class I~II laboratories. Also, the immunoassay method of the present invention is configured to assay an NSP antibody so as to identity a living individual infected with FMDV. As discovered by experiments, the present invention demonstrates sensitivity and specificity, both higher than 95%, indicating that the present invention has specificity to specimens infected with FMDV and is capable of distinguishing an antibody produced by a naturally infected animal from an antibody produced by a vaccine-immunized animal.

The present invention provides a hybridoma cell line CmA40 as deposited under American Type Culture Collection ("ATCC") located at 10801 University Boulevard, Manassas, Va. 20110, USA, deposited Sep. 14, 2010, and given the ATCC patent deposit number PTA-11304, characterized in that the hybridoma cell line CmA40 is produced by cell fusion of a parental cell and a myeloma cell line. The parental cell is a splenocyte isolated from the spleen of a mouse immunized by an antigen derived from a 3ABC non-structural protein of FMDV. The antigen is expressed by a prokaryotic cell. The monoclonal antibody produced by the hybridoma cell line can specifically recognize a 3ABC polypeptide of FMDV but does not cross-react with an antiserum of swine vesicular disease virus (SVDV).

Hence, it is a major objective of the present invention to provide a hybridoma cell line, such that a monoclonal antibody produced by the hybridoma cell line can specifically recognize an NSP of FMDV but does not cross-react with antibodies specific to any other vesicular diseases, thereby allowing the hybridoma cell line to be used in the development of a reagent for quick immunoassay.

The present invention further provides a monoclonal antibody, characterized in that the monoclonal antibody is produced from the cell line CmA40 as deposited under American Type Culture Collection patent deposit number PTA-11304 and can specifically recognize the NSP 3ABC polypeptide of FMDV but does not cross-react with antibodies against SVDV.

Accordingly, it is another major objective of the present invention to provide a monoclonal antibody that specifically recognizes the NSP of FMDV but does not cross-react with antibodies specific to any other vesicular diseases, such that the monoclonal antibody is fit for the development of a reagent for quick immunoassay.

The present invention further provides an immunoassay reagent and kit including the aforesaid monoclonal antibody and an immunoassay method using the monoclonal antibody, wherein the monoclonal antibody specifically recognizes the 3ABC polypeptide of FMDV but does not cross-react with antibodies specific to any other vesicular diseases, such that the monoclonal antibody is fit for the development of a reagent for quick immunoassay.

BRIEF DESCRIPTION OF THE DRAWING

FIG. 1 is a schematic view of sandwich ELISA.

DETAILED DESCRIPTION OF THE EMBODIMENTS

The present invention discloses a hybridoma cell line, a monoclonal antibody therefrom, and an immunoassay reagent and kit prepared by means of the monoclonal antibody. Since the immunological principles, as well as the techniques related to cell culture, staining, and protein assays, employed in the present invention are comprehensible to persons ordinarily skilled in the art, a detailed description of such principles and techniques is omitted herein. Besides, the accompanying drawing is a schematic view of technical features of the present invention and hence does not, and need not, show the technical features thoroughly and precisely.

In the first embodiment of the present invention, a hybridoma cell line produces a monoclonal antibody specific to foot-and-mouth disease virus by a mechanism shown in FIG. 1. Referring to FIG. 1, the hybridoma cell line CmA40 as deposited under American Type Culture Collection patent deposit number PTA-11304 is produced by cell fusion of an Sp2/0 myeloma cell line and a parental cell from a BALB/c mouse. The monoclonal antibody produced by the hybridoma cell line CmA40 as deposited under American Type Culture Collection patent deposit number PTA-11304 can specifically recognize a non-structural protein (NSP) of the O/TAW/99 FMDV strain.

The parental cell that yields the hybridoma cell line CmA40 as deposited under American Type Culture Collection patent deposit number PTA-11304 is prepared by the following steps:

Step 1: Appropriate primers are designed, and an NSP 3ABC gene fragment of the O/TAW/99 FMDV strain is amplified by reverse transcription polymerase chain reaction (RT-PCR). The target gene fragment to be amplified is preferably a highly conserved region of the 3ABC gene fragment that has a nucleic acid sequence shown in SEQ ID NO:1 and an amino acid sequence shown in SEQ ID NO:2.

Step 2: The 3ABC gene fragment obtained from the reverse transcription polymerase chain reaction in Step 1 is transferred to a pET carrier. Upon confirmation of the sequence, the 3ABC gene fragment is cut by a restriction enzyme, and the gene segment thus obtained is transferred to a pTH 162-B carrier. Then, the pTH 162-B carrier thus constructed is transferred to a prokaryotic cell so as for the prokaryotic cell to express a 3ABC recombinant protein of the pTH 162-B. The prokaryotic cell used in this step is derived preferably from *E. coli*.

Step 3: The 3ABC recombinant protein expressed by the prokaryotic cell in Step 2 is purified and then used as an antigen. The purified recombinant protein is repeatedly injected into a BALB/c mouse so as for the BALB/c mouse to generate an immune response to the recombinant protein. Then, a splenocyte isolated from the spleen of the immunized BALB/c mouse is treated as a parental cell for producing a hybridoma cell line that produces an anti-FMDV NSP monoclonal antibody.

The parental cell obtained from the above steps is fused with the myeloma cell line to obtain the hybridoma cell. Then, the supernatant of the hybridoma cell culture is screened by indirect enzyme-linked immunosorbent assay (indirect ELISA) and Western blotting for a hybridoma cell line that specifically reacts with the 3ABC recombinant protein of the O/TAW/99 strain.

The hybridoma cell line obtained from the foregoing screening process produces a monoclonal antibody that can specifically recognize an NSP of the O/TAW/99 FMDV strain. The NSP includes a peptide segment coded by the highly conserved region of the 3ABC gene fragment.

In the second preferred embodiment of the present invention, a monoclonal antibody is produced by the hybridoma cell line CmA40 as deposited under American Type Culture Collection patent deposit number PTA-11304. The monoclonal antibody produced by the hybridoma cell line CmA40 as deposited under American Type Culture Collection patent deposit number PTA-11304 can specifically recognize the NSP of the O/TAW/99 strain, which is a serotype O FMDV. More particularly, the monoclonal antibody can specifically recognize a peptide segment coded by the highly conserved region of the 3ABC gene fragment of the NSP but does not cross-react with SVDV antibodies.

Since the antigen that is used to prepare the monoclonal antibody of the second preferred embodiment is derived from a recombinant protein coded by the highly conserved region of the 3ABC gene fragment of the NSP of the O/TAW/99 FMDV strain, it is revealed by the findings of subsequent experiments that the monoclonal antibody provided in the second preferred embodiment can also recognize serotype A, C, Asia 1, SAT 1, SAT 2, and SAT 3 FMDV.

A monoclonal antibody of high concentration and high purity can be obtained in the following two ways: (1) a large amount of the hybridoma cell line provided in the first preferred embodiment is cultured by an in vitro cell culture technique, and then a culture supernatant of the hybridoma cell line is collected. (2) Alternatively, the hybridoma cell line provided in the first preferred embodiment is injected into the abdomen of a mouse, and then the ascitic fluid produced is collected. The monoclonal antibody provided in the second preferred embodiment can be obtained through an appropriate purification process (for example, by means of a protein A column), using the supernatant collected from in vitro cell culture or the ascitic fluid collected from a mouse.

In the third preferred embodiment of the present invention, an immunoassay reagent is used in ELISA so as to assay an antibody under test. The immunoassay reagent includes the monoclonal antibody illustrated in the second preferred embodiment. In the third preferred embodiment, the monoclonal antibody that is included in the immunoassay reagent is produced from a parental cell, and the parental cell is previously a splenocyte isolated from the spleen of an immunized mouse; hence, the monoclonal antibody is an immunoglobulin G (IgG) of the mouse. As a result, the immunoassay reagent, when used in sandwich ELISA and coupled with another appropriate reagent, is capable of assaying a swine specimen under test and determining whether the swine specimen under test contains an anti-3ABC antibody specific to FMDV.

In the fourth preferred embodiment of the present invention, an immunoassay kit is configured to assay a swine specimen and determine whether the swine specimen contains an anti-3ABC antibody specific to FMDV, using sandwich ELISA. In the fourth preferred embodiment, the immunoassay kit includes:

(1) a monoclonal antibody which can specifically recognize a 3ABC polypeptide segment of the NSP of the O/TAW/99 FMDV strain, as does the monoclonal antibody in the second preferred embodiment, and which is coated, at an appropriate concentration, on a solid-phase carrier, wherein the solid-phase carrier is a microplate, a microsphere, a hybridization membrane, or an indicator paper;

(2) a detection reagent including a detection antibody and a signal-generating substance, wherein the detection antibody can be directly conjugate-bonded to the signal-generating substance; wherein the signal-generating substance is a radioactive marker, a phosphorescent marker, a luminescent marker (chemiluminescent marker or bioluminescent marker), a fluorescent marker, or an enzyme; wherein enzymes fit for use in the fourth preferred embodiment are hydrogen peroxidase, horseradish peroxidase (HRP), alkaline phospatase (AP), and beta-galactosidase; and wherein if an enzyme functions as the signal-generating substance, the detection antibody will be conjugate-bonded to a biotin, and the signal-generating substance in the form of enzyme will be connected to an avidin; and (3) a sample antigen derived from a recombinant protein coded by the highly conserved region of the 3ABC gene fragment of the NSP of the O/TAW/99 FMDV strain.

In the fourth preferred embodiment, the immunoassay kit further includes a substrate for reacting with an enzyme so as to undergo a color reaction. The type of the substrate correlates with the enzymatic system used in the immunoassay kit. For example, if the enzyme used is HRP, the substrate should preferably be ABTS (2,2'-azino-di(3-ethylbenzthiazoline-6-sulfonate)); if the enzyme used is AP, the substrate should preferably be para-nitrophenylphosphate (PNPP) dissolved in a diethanolamine (DEA) buffer solution.

In the fourth preferred embodiment, the immunoassay kit further includes a wash reagent for rinsing any monoclonal antibody not attached to the solid-phase carrier or for extracting, by rinsing, the sample antigen not specifically binding with the monoclonal antibody, impurity of a specimen under test, the detection antibody, and/or the signal-generating substance so as to prevent the aforesaid substances from lingering on. If left unrinsed, the aforesaid substances may cause an error to the result of an immunoassay conducted with the immunoassay kit or even contribute to a false positive result thereof. The wash reagent includes a phosphate-buffered saline (PBS), a tris (hydroxymethyl)aminomethane buffer solution (TBS), Tween 20, or a combination thereof.

In the fourth preferred embodiment, the immunoassay kit further includes a blocking reagent for blocking sites on the solid-phase carrier that are not bound with the monoclonal antibody, so as to prevent the generation of a false positive signal which may otherwise be triggered if a sample antigen, a specimen under test, a detection antibody, and/or a signal-generating substance subsequently added is attached to the immunoassay kit. The blocking reagent preferably includes a protein selected from the group consisting of bovine serum albumin (BSA), casein, and animal gelatin, or a combination thereof. Also, skimmed cow's milk can directly function as the blocking reagent in the fourth preferred embodiment.

The present invention further provides an immunoassay method for assaying an antibody under test by ELISA, as illustrated in the fifth preferred embodiment described below. Referring to FIG. 1 for a schematic view of a method for performing sandwich ELISA according to the fifth preferred embodiment, the immunoassay method includes the following steps:

Step 1: Provide a solid-phase carrier 10.

Step 2: Provide a monoclonal antibody 11. The monoclonal antibody 11 has the same characteristics as the monoclonal antibody provided in the second preferred embodiment, is produced by the hybridoma cell line CmA40 as deposited under American Type Culture Collection patent deposit number PTA-11304, can specifically recognize the NSP of the serotype O O/TAW/99 FMDV strain, and, in particular, can specifically recognize a peptide segment coded by the highly conserved region of the 3ABC gene fragment of the NSP.

Step 3: Apply the monoclonal antibody 11 provided in Step 2 to the solid-phase carrier 10.

Step 4: Provide a sample antigen 12. The sample antigen 12 binds specifically with the monoclonal antibody 11 provided in Step 2. The sample antigen 12 is preferably derived from the NSP of the O/TAW/99 FMDV strain and is more preferably derived from a 3ABC recombinant protein of the O/TAW/99 FMDV strain.

Step 5: Provide a specimen under test 13. The specimen under test 13 is applied to the solid-phase carrier 10. The specimen under test 13 controllably undergoes an immune reaction with the sample antigen 12 provided in Step 4, such that the monoclonal antibody 11, the sample antigen 12, and the specimen under test 13 jointly form an immune complex on the solid-phase carrier 10.

Step 6: Provide a detection reagent which controllably undergoes an immune reaction with the immune complex formed in Step 5, so as to generate a signal.

Step 7: Detect the signal generated in Step 6.

In addition, in the fifth preferred embodiment, the detection reagent provided in Step 6 further includes a detection antibody 14 and a signal-generating substance 15. The detection antibody 14 and the signal-generating substance 15 in the fifth preferred embodiment are substantially the same as those in the fourth preferred embodiment in terms of their characteristics, connection, and types. Therefore, a detailed description of the detection antibody 14 and the signal-generating substance 15 is omitted herein for the sake of brevity.

In the fifth preferred embodiment, the immunoassay method further includes a step of providing a wash reagent. The wash reagent rinses and thereby extracts the monoclonal antibody 11 not attached to the solid-phase carrier 10 in Step 3, the sample antigen 12 not specifically binding with the monoclonal antibody 11 in Step 4, impurity of the specimen under test 13 provided in Step 5, and the detection antibody 14 and signal-generating substance 15 not having an immune reaction with the immune complex (formed in Step 5) in Step 6, so as to prevent the aforesaid substances from lingering on. If left unrinsed, the aforesaid substances may cause an error to the result of an immunoassay using the immunoassay method or even contribute to a false positive result thereof. The wash reagent includes a PBS, a TBS, Tween 20, or a combination thereof.

If the detection reagent provided in Step 6 includes an enzyme that functions as the signal-generating substance 15, it will be necessary to add a substrate 16 capable of having an immune reaction with the enzyme provided. For example, if HRP is used as the signal-generating substance 15, ABTS should be used as the substrate 16; if AP is used as the signal-generating substance 15, the substrate 16 is preferably PNPP dissolved in DEA solvent. Also, depending on the types of the enzyme and substrate provided in Step 6, different detection methods should be used to determine the signals generated by the different enzyme-substrate systems. For example, a color reaction system including HRP as enzyme and ABTS as substrate is assayed by means of the absorption spectrum of the specimens under test at a wavelength of 450 nm or 460 nm. Likewise, a color reaction system including AP as enzyme and PNPP plus DEA as substrate is assayed by means of the absorption spectrum of the specimens under test at a wavelength of 430 nm.

The fifth preferred embodiment further includes a step of providing a blocking reagent for blocking sites on the solid-phase carrier that are not bound with the monoclonal antibody in Step 3, so as to prevent the generation of a false positive signal which may otherwise be triggered if the sample antigen, the specimen under test, the detection antibody, and/or the signal-generating substance subsequently added in Steps 4, 5, and 6 is directly attached to the solid-phase carrier 10. The blocking reagent preferably includes a protein selected from BSA, casein, animal gelatin, or a combination thereof. Also, skimmed cow's milk can directly function as the blocking reagent in the fifth preferred embodiment.

The following experiments are provided for further illustrating the present invention rather than limiting the present invention.

Experiment 1

Materials and Methods 1.1: Serum

To evaluate the sensitivity of immunoassays, 32 FMD-positive swine serum samples were collected from 8-week-old swine on the $34^{th}$ days after the swine's experimental infection with the O/TAW/97 FMDV strain.

To compare the sandwich ELISA immunoassay kit of the present invention with three commercially available ELISA immunoassay kits, a total of 320 serum samples were collected from 32 specific-pathogen-free (SPF) swine which had been experimentally infected with the O/TAW/97 FMDV strain. The 320 serum samples were collected on the $0^{th}$ day, $2^{nd}$ day, $4^{th}$ day, $6^{th}$ day, $8^{th}$ day, $10^{th}$ day, $14^{th}$ day, $21^{st}$ day, $28^{th}$ day, and $34^{th}$ day after the swine's experimental infection with the O/TAW/97 FMDV strain. In addition, 30 serum samples were collected from swine infected with the O/TAW/97 FMDV strain on the $28^{th}$ day after the swine's experimental infection.

To assay specificity, 255 serum samples were collected from uninfected swine, and 165 serum samples were collected from vaccinated swine. Of the 255 serum samples collected from uninfected swine, 96 were collected from SPF swine, and the remaining 159 serum samples were collected from uninfected swine before the FMD epidemic in 1997. The vaccinated swine from which the aforesaid 165 serum samples were collected were uninfected and had been administrated twice with commercially available serotype O FMDV vaccine.

To evaluate possible cross-reactivity demonstrated by the sandwich ELISA immunoassay kit of the present invention toward swine vesicular disease virus (SVDV) and to affirm cross-reactivity demonstrated by the sandwich ELISA immunoassay kit of the present invention toward FMDV of different serotypes, the experiment used six anti-SVDV antisera (UKG/27/72 strain, EU SVD reference serum batch 2002) and six bovine antisera specific to FMDV of different serotypes (serotypes A, C, Asia 1, SAT 1, SAT 2, and SAT 3), produced by the Institute for Animal Health, Pirbright, the United Kingdom.

Sera were collected from the swine which had been experimentally infected with the O/TAW/97 strain and the O/TAW/99 strain, respectively, on the $28^{th}$ day after infection (that is, during the convalescence period). The serum neutralizing antibody titers (SN titers) of the sera collected from the swine experimentally infected with the O/TAW/97 strain and the O/TAW/99 strain are 1:256 and 1:512, respectively. The sera were used as the positive control group in Western blotting and the sandwich ELISA. The negative control group consisted of the SPF swine sera.

1.2: Design of RT-PCR Primers

A primer pair was designed to amplify a nucleic acid fragment of the 3ABC gene region of the genome of the O/TAW/99 FMDV strain. (The nucleic acid fragment is nucleotide regions No. 5595 to No. 6119 of GenBank accession No. AJ539137. See SEQ ID NO:1 for a detailed sequence, and see SEQ ID NO:2 for its amino acid sequence.) The sequence of the forward primer shown in SEQ ID NO:3 is as follows: 5'-CACCGGATCCTGTCGCGAGACTCGCAA-GAGACAGCAG-3', which includes a restriction site for the BamHI restriction enzyme. The sequence of the reverse primer shown in SEQ ID NO:4 is as follows: 5'-CCCGAAT-TCGCACGTCTTCCCGTCGAGGATGAGCTC-3', which includes a restriction site for the EcoRI restriction enzyme.

1.3: RT-PCR

A mixture for use in RT-PCR was prepared from the Superscript™ One-Step RT-PCR System and Platinum® Pfx DNA Polymerase. The reaction took place in a GeneAmp PCR system 2400 thermocycler. The temperature and timing of the reaction are as follows. First, a reaction sample was cultured at 42° C. for 40 minutes. Next, the reaction sample underwent pre-denaturation at 90~95° C. for 50 seconds. Then, the reaction sample underwent the following thermal cycle repeatedly, that is, 30 to 40 times: denaturation at 90~95° C. for 30 seconds; annealing at 50~55° C. for 30 seconds; and extension at 68~72° C. for one minute. Finally, the reaction sample was extended at 72° C. for 7 minutes and then kept at 4° C. The RT-PCR product was preserved at −20° C. until its use in subsequent experiments. 10 μL of the RT-PCR product was assayed by 2% agarose gel electrophoresis, stained with the SYBR Safe™ DNA gel stain in a 1× TAE buffer solution, and colored in the presence of UV light.

1.4: Cloning of the 3ABC Gene of FMDV

A product in agarose gel was purified and extracted, using the Gel/PCR DNA Fragments Extraction Kit. The purified and extracted product was processed by appropriate restriction enzymes (BamHI and EcoRI) and then annealed with a pET vector so as to produce a complete expression vector. The expression vector was transferred to a competent cell BL21 (DE3) and cultured in a Luria-Bertani agarose petri dish containing 100 μg/mL of ampicillin Positive colonies were selected. Then, plasmids were extracted from the colonies with the Miniprep Kit. Following that, the plasmid samples carrying the 3ABC gene fragments were selected. Last, the selected samples underwent DNA sequencing so as to identify the nucleic acid sequence of the 3ABC gene fragments carried by the plasmid samples.

1.5: Expression and Purification of FMDV 3ABC Polypeptide in *E. coli*

*E. coli* was transformed by means of the pTH 162-B plasmid produced and then vigorously shaken at 37° C. inside a Luria-Bertani culture solution containing 100 μg/mL of ampicillin, so as for the *E. coli* to be cultured therein. In the mid-logarithmic phase of culture, isopropylthiogalactoside (IPTG) was added to the culture solution, such that the final concentration of *E. coli* was 1 mM. Then, the culture of *E. coli* continued for another four hours so as to induce the expression of 3ABC polypeptide. Afterward, *E. coli* bacteria were collected by centrifugation. The collected *E. coli* bacteria were decomposed by introduction of a bacterial protein extraction reagent (B-PER) or by ultrasonic vibration. The soluble 3ABC polypeptide found in the decomposed *E. coli* bacteria was purified by a His-Tag affinity chromatography column, and then the purified product is quantified.

1.6: SDS Gel Electrophoresis and Western Blotting

The 3ABC polypeptide obtained by purification in Experiment 1.5 was assayed by 12% SDS gel electrophoresis. After that, the molecular weight of the protein was displayed on a PVDF filter paper or a nitrocellulose filter paper. Then, reactivity of the protein toward strongly positive swine sera was analyzed by Western blotting, which was conducted by: providing a properly diluted positive swine serum as a primary antibody; providing a properly diluted AP-containing goat anti-swine IgG as a secondary antibody; and providing 5-bromo-4-chloro-3-indolyl phosphate and nitro blue tetrazolium as a substrate for AP and a coloring substance, respectively.

1.7: Virus Neutralization Test

To identify the severity of experimental infection of the swine in the positive serum group, all the sera collected from the swine infected with FMDV underwent virus neutralization test, using the method set forth in the Manual of Diagnostic Tests and Vaccines for Terrestrial Animals published by the Office International Des Epizooties (OIE).

1.8: Mouse Immunization and Production of Anti-3ABC Monoclonal Antibody

A hybridoma cell line producing anti-3ABC recombinant protein monoclonal antibody was produced in the following way. As an antigen, 200 μg of the 3ABC recombinant protein produced in Experiment 1.5 was administered, via hypodermal injection, to a BALB/c mouse so as to immunize the BALB/c mouse. The interval of immunization was four weeks. Three to four days before cell fusion, the same amount of the antigen was added to a PBS, and the antigen-containing PBS was administered, by hypodermal injection, to the mouse as a boost injection. Afterward, the immunized BALB/c mouse was humanely killed, and the spleen was removed from the carcass. A splenocyte isolated from the spleen underwent cell fusion with the Sp2/0 myeloma cell line, thereby producing the hybridoma cell. Two weeks later, the culture supernatant of the hybridoma cell was screened by indirect ELISA, which was based on O/TAW/97 or O/TAW/99 FMDV recombinant protein. Also, the culture supernatant of the hybridoma cell was screened by Western blotting, using the same steps taken in Experiment 1.6. Upon completion of the indirect ELISA, the hybridoma cell line with a positive/negative (P/N) ratio greater than 2 was selected to undergo scale-up culture. When determined to be capable of producing an anti-3ABC antibody, the hybridoma cell line was injected into the abdomen of a BALB/c mouse, and the resultant ascitic fluid was collected. Last, the collected ascitic fluid was purified by an Affi-Gel protein A column so as to extract the antibody. The maximum concentration of the purified antibody was 10 mg/mL 1.9: Sandwich ELISA The sandwich ELISA (shown in FIG. 1) specific to serotype O FMDV was configured to quantify the antiserum of FMDV NSP. A microplate (Nunc Maxisorb) was coated with the monoclonal antibody, using a carbonic-acid/bicarbonate buffer solution of pH 9.6 and a concentration of 0.06M as a coating buffer solution. After the coating process, the monoclonal antibody was cultured at 4° C. until the next morning. The microplate was coated with the monoclonal antibody by checkerboard titration, so as to determine the optimal concentration of the monoclonal antibody for the NSP of serotype O FMDV. Upon completion of the coating process, an RNSP of serotype O FMDV optimal diluted with a diluting solution was added to the microplate and incubated therein at 37° C. for one hour. Then, 100 μL of a swine serum properly diluted with a blocking buffer solution was added to the microplate and incubated therein at 37° C. for one hour. 100 μL of HRP-conjugated goat-anti-swine IgG diluted with a blocking buffer solution was added to the wells of the microplate. Then, 3,3',5,5'-tetramethylbenzidine (TMB) was used as a substrate and allowed to undergo a color reaction at room temperature for 10 to 15 minutes. Last, 50 μL of 1.0M sulfuric acid was added to each of the wells to stop the color reaction, and the $OD_{450\ nm}$ readings in the wells were taken. In the aforesaid steps, all those substances that were incubated at 37° C. for one hour were subsequently rinsed with a rinsing solution six times.

1.10: Comparison of ELISA Kits for Assaying Anti-FMDV NSP Antibody

A comparative analysis was conducted to compare the capabilities of three commercially available anti-FMDV NSP antibody detecting ELISA kits with the immunoassay kit of the present invention. Ceditest FMDV-NS kit (Cedi-Diagnostics B.V., Lelystad, Netherlands) is a blocking ELISA kit. UBI FMD NS EIA kit (United Biomedical Inc., Hauppauge, N.Y., USA) is an indirect ELISA kit using a synthetic 3B peptide. CHEKIT FMD-3ABC kit (IDEXX Laboratories Inc., Westbrook, Me., USA) is an indirect ELISA kit using a 3ABC polypeptide expressed by *E. coli*. The aforesaid immunoassay kits were used in accordance with the instruction manuals provided by manufacturers.

Experiment 2

3ABC Recombinant Protein Expressed by *E. coli*

The 3ABC genetic sequence of the O/TAW/99 FMDV was obtained from the GenBank of the National Center for Biotechnology Information (NCBI) of the United States. See SEQ ID NO:1 for a detailed sequence of nucleotide regions No. 5595 to No. 6119 of GenBank accession No. AJ539137, which includes a coding region with a length of 525 nucleotides, and thus the recombinant protein coded thereby is composed of 175 amino acids (of a sequence shown in SEQ ID NO:2). A comparison of the genetic sequences of Pan-Asia serotype O FMDV strains recently isolated from Asia, Africa, and Europe shows approximately 97% to 99% genetic identity.

A primer pair was designed to amplify a nucleic acid fragment of the 3ABC gene region. The sequence of the forward primer shown in SEQ ID NO:3 is as follows: 5'-CACCG-GATCCTGTCGCGAGACTCGCAAGAGACAGCAG-3', which includes a restriction site for the BamHI restriction enzyme. The sequence of the reverse primer shown in SEQ ID NO:4 is as follows: 5'-CCCGAATTCGCACGTCTTC-CCGTCGAGGATGAGCTC-3', which includes a restriction site for the EcoRI restriction enzyme. The coding region with a length of 525 nucleotides was amplified using the primer pair and the RT-PCR method. RT-PCR took place in a Gene-Amp PCR system 2400 thermocycler. The temperature and time of the reaction are as follows. First, a reaction sample was incubated at 42° C. for 40 minutes. Then, the reaction sample underwent pre-denaturation at 90~95° C. for 50 seconds. Following that, the reaction sample underwent the following thermal cycle repeatedly, that is, 30 to 40 times: denaturation at 90~95° C. for 30 seconds; annealing at 50~55° C. for 30 seconds; and extension at 68~72° C. for one minute. Finally, the reaction sample was extended at 72° C. for 7 minutes and then kept at 4° C. The RT-PCR product was stored at −20° C. until its use in subsequent experiments.

A DNA fragment obtained by the RT-PCR enabled amplification was inserted into a pET vector so as to produce a complete expression vector. The expression vector was transferred to the competent cell BL21 (DE3) of *E. coli* and then cultured in a Luria-Bertani agarose petri dish containing 100 μg/mL of ampicillin. After positive colonies were selected, plasmids carrying the inserted 3ABC gene fragment were extracted from the colonies.

The plasmids carrying the inserted 3ABC gene fragment were transferred to *E. coli* BL21 (DE3) so as to transform the *E. coli*. Then, the *E. coli* was vigorously shaken at 37° C. in a Luria-Bertani culture solution containing 100 μg/mL of ampicillin, so as for the *E. coli* to be cultured therein. In the mid-logarithmic phase of culture, IPTG was added to the culture solution to the final concentration of 1 mM. Then, the culture of *E. coli* continued for another four hours so as to induce the expression of 3ABC recombinant protein. The expressed 3ABC recombinant protein was purified by an affinity chromatography column. After that, the purified 3ABC recombinant protein was assayed by 12% SDS gel electrophoresis and Western blotting. According to the assay results of Western blotting, the protein thus expressed was 40 kDa in size and was proved to be capable of undergoing an immune reaction with an anti-FMDV antiserum (not shown). The concentration of the 3ABC recombinant protein after purification was approximately 11.2 mg/mL, when quantified.

Experiment 3

Mouse Immunization and Production of Anti-3ABC Monoclonal Antibody

A hybridoma cell line producing an anti-3ABC recombinant protein monoclonal antibody was produced in the following manner. As an antigen, 200 μg of the 3ABC recombinant protein produced in Experiment 1.5 was administered, by hypodermal injection, to a BALB/c mouse to immunize the BALB/c mouse. The interval of immunization was four weeks. Three to four days before cell fusion, the same amount of the antigen was added to a PBS, and the antigen-containing PBS was administered, by hypodermal injection, to the mouse as a boost injection. Afterward, the immunized BALB/c mouse was humanely killed, and the spleen was removed from the carcass. A splenocyte isolated from the spleen underwent cell fusion with the Sp2/0 myeloma cell line, thereby producing the hybridoma cell. Two weeks later, the culture supernatant of the hybridoma cell was screened by indirect ELISA, which contained O/TAW/97 or O/TAW/99 FMDV recombinant protein. In addition, the culture supernatant of the hybridoma cell was screened by Western blotting, using the same steps taken in Experiment 1.6. Upon completion of the indirect ELISA, the hybridoma cell line with a positive/negative (P/N) ratio greater than 2 was selected to undergo scale-up culture. When determined to be capable of producing an anti-3ABC antibody, the hybridoma cell line was injected into the abdomen of a BALB/c mouse, and the resultant ascitic fluid was collected. Last, the collected ascitic fluid was purified by an Affi-Gel protein A column (Millipore) so as to extract the antibody. The maximal concentration of the purified antibody was 10 mg/mL.

Experiment 4

Interpretation of Readings Taken in Sandwich ELISA

To ensure the quality and stability of the results of immunoassays performed on sera, each sandwich ELISA was performed twice with the 96-well microplate, regardless of whether the sera were positive or negative. As revealed by the statistical analysis of the findings of 18 assays, the assay results of the positive sera is 0.90±0.09, with a coefficient of variation of 9.78%; on the other hand, the assay results of the negative sera is 0.09±0.02, with a coefficient of variation of 24.33%. A total of 770 serum $OD_{450\ nm}$ readings were obtained and standardized for presentation. The 287 negative swine serum samples, of which 255 were collected from uninfected swine and the remaining 32 serum samples were collected from infected swine on the $0^{th}$ day after infection. The cut-off value of the results of the sandwich ELISA provided by the present invention was determined by the 287 negative serum samples and 62 sera from experimentally infected swine.

The evaluation of specificity of the immunoassay kit of the present invention entailed assaying serums sampled from 96 SPF swine. All the samples under test yielded $OD_{450\ nm}$ readings less than 0.15, wherein only a portion of the samples under test yielded $OD_{450\ nm}$ readings greater than the range of 0.06 to 0.11. Besides, all the $OD_{450\ nm}$ readings corresponding to serums sampled from vaccine-inoculated swine are less than 0.22. Hence, the cut-off value of $OD_{450\ nm}$ readings is determined at 0.22. In other words, the immunoassay result is deemed negative when the $OD_{450\ nm}$ readings of a specimen under test is less than 0.22, and the immunoassay result is deemed positive when the $OD_{450\ nm}$ readings of a specimen under test is equal to or greater than 0.22. The assay results are shown in Table 1.

TABLE 1

| Range of $OD_{450nm}$ readings | Not infected (Naïve) | | | Experimental non-infection | |
|---|---|---|---|---|---|
| | Before outbreak [a] | SPF [a] | Vaccinated [a] | (0 day after infection) [a] | Experimental infection [b, c] |
| 0-0.05 | 1 | 7 | 100 | 1 | 0 |
| 0.06-0.11 | 108 | 80 | 40 | 31 | 0 |
| 0.12-0.17 | 46 | 9 | 14 | | 0 |
| 0.18-0.23 | 4 (<0.22) | | 11 (<0.22) | | 1 (=0.22) |
| 0.24-0.29 | | | | | 4 |
| 0.30-0.35 | | | | | 2 |
| 0.36-0.41 | | | | | 3 |
| 0.42-0.47 | | | | | 5 |
| 0.48-0.53 | | | | | 7 |
| 0.54-0.59 | | | | | 6 |
| 0.60-0.65 | | | | | 4 |
| 0.66-0.71 | | | | | 9 |
| 0.72-0.77 | | | | | 3 |
| 0.78-0.83 | | | | | 8 |
| 0.84-0.89 | | | | | 1 |
| 0.90-0.95 | | | | | 2 |
| 0.96-1.01 | | | | | 4 |
| 1.02-1.07 | | | | | 1 |
| 1.08-1.13 | | | | | 0 |

TABLE 1-continued

| Range of $OD_{450nm}$ readings | Not infected (Naïve) | | | Experimental non-infection | |
|---|---|---|---|---|---|
| | Before outbreak [a] | SPF [a] | Vaccinated [a] | (0 day after infection) [a] | Experimental infection [b, c] |
| 1.14-1.19 | | | | | 0 |
| >1.20 | | | | | 2 |
| Total | 159 | 96 | 165 | 32 | 62 |

[a] Immunoassay result regarded as negative if $OD_{450nm}$ readings < 0.22.
[b] Immunoassay result regarded as positive if $OD_{450nm}$ readings ≥ 0.22.
[c] Serum sampled from 30 swine on the 14$^{th}$ day after infection.

Experiment 5

Test on Reaction Kinetics of the Antibody of the Present Invention in Binding with the Antigenic Determinant Sites on 3ABC Antigen The successively sampled positive swine sera were assayed by the immunoassay kit of the present invention and the aforesaid three commercially available ELISA kits. According to assay results obtained with the immunoassay kit of the present invention, an antibody specific to 3ABC antigen can be discovered in sera sampled from 32 swine on the 8$^{th}$ day after infection, and the immunoassay kit of the present invention produced a positive result on the presence of an antibody specific to 3ABC antigen in sera sampled from the swine on the 10$^{th}$ day after infection. In addition, with the immunoassay kit of the present invention, the positive rate of the entire experiment is higher than 90%. Also, 14 days after their experimental infection, all the swine manifested an SN titer greater than 1:16 or even as high as 1:1024. The test results are shown in Table 2.

TABLE 2

| SN titer | Number of Days after Infection | | | | | | | | | |
|---|---|---|---|---|---|---|---|---|---|---|
| | 0 | 2 | 4 | 6 | 8 | 10 | 14 | 21 | 28 | 34 |
| ≦1:3 | 30 | 31 | 13 | 1 | | | | | | |
| 1:4 | 1 | | 12 | 3 | 2 | 1 | | | | |
| 1:8 | 1 | 1 | 6 | 6 | 4 | 3 | | | | |
| 1:16 | | | 1 | 5 | 12 | 16 | 3 | 1 | | |
| 1:32 | | | | | 13 | 7 | 7 | 9 | 4 | 1 |
| 1:64 | | | | 4 | 6 | 5 | 12 | 4 | 2 | 2 |
| 1:128 | | | | | | | 7 | 9 | 7 | 6 |
| 1:256 | | | | | 1 | | 1 | 9 | 12 | 13 |
| 1:512 | | | | | | | | 4 | 8 | 7 |
| 1:1024 | | | | | | | | 1 | 3 | 3 |
| ≧1:16 | 0 | 0 | 1 | 22 | 26 | 28 | 32 | 32 | 32 | 32 |

The test results shown in Table 2 confirm that the swine used in the experiment were infected. The commercially available Ceditest immunoassay kit and UBI immunoassay kit yielded results similar to those in the present experiment whenever the same serum samples were used, but this is not true of the CHEKIT immunoassay kit. According to the assay results obtained with the CHEKIT immunoassay kit, an NSP antibody was detected in the swine sera sampled on the 14$^{th}$ day after infection, and the positive rate of the entire experiment is not higher than 80%. The assay results obtained with the immunoassay kit of the present invention and the Ceditest FMDV-NS immunoassay kit from the same serum samples are shown in Table 3. The assay results obtained with the two immunoassay kits show 97.2% (311/320) agreement, with a kappa statistic of 0.94.

TABLE 3

| Immunoassay reagent and kit of the present invention | Ceditest immunoassay reagent and kit | | |
|---|---|---|---|
| (Sandwich ELISA) | Positive | Negative | Total |
| Positive | 175 | 6 | 181 |
| Negative | 3 | 136 | 139 |
| Total | 178 | 142 | 320 |

Kappa: 0.943, agreement: 0.972, standard deviation: 0.019 95% confidence interval: lower limit: 0.906, upper limit: 0.98

Experiment 6

Comparison Between the Immunoassay Kit of the Present Invention and Commercially Available ELISA Kits The immunoassay kit of the present invention has sensitivity of 98.4% to infected swine and specificity of 100% toward uninfected swine and vaccinated swine, as revealed by the experiment. The findings of a comparison between the immunoassay kit of the present invention and the commercially available ELISA kits are shown in Table 4.

TABLE 4

| Immunoassay kit | Sensitivity | | Specificity | |
|---|---|---|---|---|
| | Positive serum (experimental infection)[a] | Negative serum (SPF) | Negative serum (before FMD outbreak) | Serum from vaccinated swine |
| Immunoassay kit of the present invention | 98.4% (61/62) | 100% (96/96) | 100% (159/159) | 100% (165/165) |
| Ceditest immunoassay kit | 98.4% (61/62) | 100% (96/96) | 100% (158/158) | 100% (167/167) |
| UBI immunoassay kit | 98.4% (61/62) | 100% (96/96) | 100% (158/158) | 85.3% (93/109) |
| CHEKIT immunoassay kit | 35.5% (22/62) | 100% (96/96) | 100% (158/158) | 100% (167/167) |

[a] Sensitivity was evaluated by assaying serums sampled from 32 swine on the 14$^{th}$ day after infection.

The experiment results obtained with the immunoassay kit of the present invention are similar to those obtained with the Ceditest FMDV-NS immunoassay kit. The immunoassay kit of the present invention has specificity of 100% toward vaccinated swine, which is higher than that (85.3%) of the UBI immunoassay kit. Moreover, the immunoassay kit of the present invention has sensitivity of 98.4% toward infected swine, which is far higher than that (35.5%) of the CHEKIT immunoassay kit.

Experiment 7

Test on Specificity of the Immunoassay Kit of the Present Invention Toward FMDV of Other Serotypes in Bovine Antiserum In this experiment, sandwich ELISA was used to assay and determine whether the antibody provided by the present invention can specifically recognize serotypes A, C, Asia 1, SAT 1, SAT 2, and SAT 3 FMDV. As revealed by the experiment results, the anti-FMDV NSP antibody provided by the present invention had positive reaction with serotypes A, C, Asia 1, SAT 1, SAT 2, and SAT 3 FMDV in bovine serum, wherein the OD$_{450\,nm}$ readings corresponding to serotypes C, Asia 1, SAT 1, and SAT 3 are all greater than 0.5.

Experiment 8

Test on Specificity of the Immunoassay Kit of the Present Invention Toward SVDV Antibody Six swine antisera specific to UKG/27/72 SVDV strain were assayed by the immunoassay kit of the present invention, and the assay results were negative. Accordingly, the immunoassay reagent and kit of the present invention did not cross-react with, and therefore did not specifically recognize, the antisera specific to SVDV. That is to say, the immunoassay reagent and kit of the present invention are capable of differential diagnosis of against FMDV and SVDV antibodies.

The aforesaid embodiments merely serve as the preferred embodiments of the present invention and should not be construed as limitations on the scope of the present invention in any way. Moreover, as the contents disclosed herein should be readily understood and can be implemented by a person skilled in the art, all equivalent changes or modifications which do not depart from the spirit of the present invention should be encompassed by the appended claims.

```
                        SEQUENCE LISTING

<160> NUMBER OF SEQ ID NOS: 5

<210> SEQ ID NO 1
<211> LENGTH: 525
<212> TYPE: DNA
<213> ORGANISM: Aphthovirus O
<220> FEATURE:
<221> NAME/KEY: CDS
<222> LOCATION: (1)..(525)
<223> OTHER INFORMATION: Obtained by amplifying the 3ABC gene region of
      the genome of the O/TAW/99 foot-and-mouth disease virus strain
      through a polymerase chain reaction is equivalent to nucleotide
      regions No. 5595 to No. 6119 of GenBank accession No. AJ5391

<400> SEQUENCE: 1 cgc gag act cgc aag aga cag cag atg gtg gat gat gca gtg aac gag        48
Arg Glu Thr Arg Lys Arg Gln Gln Met Val Asp Asp Ala Val Asn Glu
1               5                   10                  15 tac att gag aag gca agc atc acc acg gat gac aag act ctt gac gag        96
Tyr Ile Glu Lys Ala Ser Ile Thr Thr Asp Asp Lys Thr Leu Asp Glu
            20                  25                  30 gcg gaa aag aac cct ctg gag acc agc ggt gcc acc act gtt ggt ttc       144
Ala Glu Lys Asn Pro Leu Glu Thr Ser Gly Ala Thr Thr Val Gly Phe
        35                  40                  45 aga gag aaa act ctc ccg gga cac aag gcg agt gat gac gtg aac tcc       192
Arg Glu Lys Thr Leu Pro Gly His Lys Ala Ser Asp Asp Val Asn Ser
    50                  55                  60 gag ccc gcc aaa ccc gtg gaa gaa caa cca caa gct gaa gga ccc tac       240
Glu Pro Ala Lys Pro Val Glu Glu Gln Pro Gln Ala Glu Gly Pro Tyr
65                  70                  75                  80 acc ggt cca ctc gag cgt caa aaa cct ctg aaa gtg aga gcc aag ctc       288
Thr Gly Pro Leu Glu Arg Gln Lys Pro Leu Lys Val Arg Ala Lys Leu
                85                  90                  95 cca cag cag gag ggg ccc tac gct ggt ccg atg gag aga cag aaa ccg       336
Pro Gln Gln Glu Gly Pro Tyr Ala Gly Pro Met Glu Arg Gln Lys Pro
            100                 105                 110 ctg aaa gtg aaa gtg aaa gcc ccg gtc gtt aag gaa gga cct tac gaa       384
Leu Lys Val Lys Val Lys Ala Pro Val Val Lys Glu Gly Pro Tyr Glu
        115                 120                 125 gga ccg gtg aag aaa cct gtc gct ttg aaa gtg aaa gca aag aac ttg       432
Gly Pro Val Lys Lys Pro Val Ala Leu Lys Val Lys Ala Lys Asn Leu
    130                 135                 140 atc gtc act gag agt ggt gct ccc ccg act gac ttg caa aag atg gtc       480
Ile Val Thr Glu Ser Gly Ala Pro Pro Thr Asp Leu Gln Lys Met Val
145                 150                 155                 160 atg ggt aac acc aag cct gtt gag ctc atc ctc gac ggg aag acg           525
Met Gly Asn Thr Lys Pro Val Glu Leu Ile Leu Asp Gly Lys Thr
                165                 170                 175
```

<210> SEQ ID NO 2
<211> LENGTH: 175
<212> TYPE: PRT
<213> ORGANISM: Aphthovirus O

<400> SEQUENCE: 2

Arg Glu Thr Arg Lys Arg Gln Gln Met Val Asp Asp Ala Val Asn Glu
1               5                   10                  15

Tyr Ile Glu Lys Ala Ser Ile Thr Thr Asp Asp Lys Thr Leu Asp Glu
            20                  25                  30

Ala Glu Lys Asn Pro Leu Glu Thr Ser Gly Ala Thr Thr Val Gly Phe
        35                  40                  45

Arg Glu Lys Thr Leu Pro Gly His Lys Ala Ser Asp Asp Val Asn Ser
    50                  55                  60

Glu Pro Ala Lys Pro Val Glu Gln Pro Gln Ala Glu Gly Pro Tyr
65                  70                  75                  80

Thr Gly Pro Leu Glu Arg Gln Lys Pro Leu Lys Val Arg Ala Lys Leu
                85                  90                  95

Pro Gln Gln Glu Gly Pro Tyr Ala Gly Pro Met Glu Arg Gln Lys Pro
            100                 105                 110

Leu Lys Val Lys Val Lys Ala Pro Val Val Lys Glu Gly Pro Tyr Glu
        115                 120                 125

Gly Pro Val Lys Lys Pro Val Ala Leu Lys Val Lys Ala Lys Asn Leu
    130                 135                 140

Ile Val Thr Glu Ser Gly Ala Pro Pro Thr Asp Leu Gln Lys Met Val
145                 150                 155                 160

Met Gly Asn Thr Lys Pro Val Glu Leu Ile Leu Asp Gly Lys Thr
                165                 170                 175

<210> SEQ ID NO 3
<211> LENGTH: 175
<212> TYPE: PRT
<213> ORGANISM: Aphthovirus O
<220> FEATURE:
<221> NAME/KEY: CHAIN
<222> LOCATION: (1)..(175)
<223> OTHER INFORMATION: polypeptide chain obtained from expression of
      pET vector

<400> SEQUENCE: 3

Arg Glu Thr Arg Lys Arg Gln Gln Met Val Asp Asp Ala Val Asn Glu
1               5                   10                  15

Tyr Ile Glu Lys Ala Ser Ile Thr Thr Asp Asp Lys Thr Leu Asp Glu
            20                  25                  30

Ala Glu Lys Asn Pro Leu Glu Thr Ser Gly Ala Thr Thr Val Gly Phe
        35                  40                  45

Arg Glu Lys Thr Leu Pro Gly His Lys Ala Ser Asp Asp Val Asn Ser
    50                  55                  60

Glu Pro Ala Lys Pro Val Glu Gln Pro Gln Ala Glu Gly Pro Tyr
65                  70                  75                  80

Thr Gly Pro Leu Glu Arg Gln Lys Pro Leu Lys Val Arg Ala Lys Leu
                85                  90                  95

Pro Gln Gln Glu Gly Pro Tyr Ala Gly Pro Met Glu Arg Gln Lys Pro
            100                 105                 110

Leu Lys Val Lys Val Lys Ala Pro Val Val Lys Glu Gly Pro Tyr Glu
        115                 120                 125

Gly Pro Val Lys Lys Pro Val Ala Leu Lys Val Lys Ala Lys Asn Leu
    130                 135                 140

```
Ile Val Thr Glu Ser Gly Ala Pro Pro Thr Asp Leu Gln Lys Met Val
145                 150                 155                 160

Met Gly Asn Thr Lys Pro Val Glu Leu Ile Leu Asp Gly Lys Thr
                165                 170                 175

<210> SEQ ID NO 4
<211> LENGTH: 37
<212> TYPE: DNA
<213> ORGANISM: Artificial Sequence
<220> FEATURE:
<223> OTHER INFORMATION: The forward primer for amplifying the 3ABC gene
      region of the genome of the O/TAW/99 foot-and-mouth disease virus
      strain.
<220> FEATURE:
<221> NAME/KEY: primer_bind
<222> LOCATION: (1)..(37)
<223> OTHER INFORMATION: The forward primer for amplifying the 3ABC gene
      region of the genome of the O/TAW/99 foot-and-mouth disease virus
      strain.

<400> SEQUENCE: 4
caccggatcc tgtcgcgaga ctcgcaagag acagcag                              37

<210> SEQ ID NO 5
<211> LENGTH: 34
<212> TYPE: DNA
<213> ORGANISM: Artificial Sequence
<220> FEATURE:
<223> OTHER INFORMATION: The reverse primer for amplifying the 3ABC gene
      region of the genome of the O/TAW/99 foot-and-mouth disease virus
      strain.
<220> FEATURE:
<221> NAME/KEY: primer_bind
<222> LOCATION: (1)..(34)
<223> OTHER INFORMATION: The reverse primer for amplifying the 3ABC gene
      region of the genome of the O/TAW/99 foot-and-mouth disease virus
      strain.

<400> SEQUENCE: 5
ccgaattcgc cgtcttcccg tcgaggatga gctc                                 34
```

What is claimed is:

1. A hybridoma cell line CmA40 as deposited under American Type Culture Collection patent deposit PTS-11304.

2. A monoclonal antibody produced by the hybridoma cell line CmA40 as deposited under American Type Culture Collection patent deposit PTS-11304.

3. An immunoassay reagent for detecting an antigen, the immunoassay reagent being characterized by comprising the monoclonal antibody of claim 2.

4. An immunoassay kit for a sandwich immunoassay to detect an anti-3ABC antibody that is specific to a foot-and-mouth disease virus (FMDV), wherein the kit comprises the monoclonal assay of claim 2 and a detection reagent.

5. The immunoassay kit of claim 4, further comprising a sample antigen derived from a 3ABC polypeptide of the foot-and-mouth disease virus (FMDV).

6. The immunoassay kit of claim 4, wherein the detection reagent comprises a detection antibody and a signal-generating substance.

7. The immunoassay kit of claim 4, further comprising a wash reagent, the wash reagent being one selected from the group consisting of a phosphate-buffered saline (PBS), a tris(hydroxymethyl)aminomethane buffer solution (TBS), and Tween 20, or a combination thereof.

8. An immunoassay method for performing an assay by enzyme-linked immunosorbent assay (ELISA), comprising steps of:
   providing a solid-phase carrier;
   providing the monoclonal antibody of claim 2;
   applying the monoclonal antibody to the solid-phase carrier;
   providing a sample antigen for binding specifically with the monoclonal antibody;
   providing a specimen that can operationally react with the sample antigen so as to form an immune complex on the solid-phase carrier;
   providing a detection reagent that can operationally react with the immune complex so as to generate a signal; and
   detecting the signal.

9. The immunoassay method of claim 8, wherein the sample antigen is derived from a 3ABC gene of a foot-and-mouth disease virus (FMDV).

10. The immunoassay method of claim 8 wherein the detection reagent comprises a detection antibody and a signal-generating substance.

* * * * *